United States Patent [19]

Cerefice et al.

[11] 4,073,794

[45] Feb. 14, 1978

[54] 7,8 DIACYL BICYCLO[2.2.2]BIS(2,3-DICARBOXIMIDE) COMPOUNDS

[75] Inventors: Steven A. Cerefice, Naperville; Ellis K. Fields, River Forest, both of Ill.

[73] Assignee: Standard Oil Company, Chicago, Ill.

[21] Appl. No.: 733,118

[22] Filed: Oct. 18, 1976

[51] Int. Cl.$^2$ ............................................ C07D 209/34
[52] U.S. Cl. .............................. 260/326 C; 260/346.3; 260/514 G; 560/127
[58] Field of Search .................................... 260/326 C

[56] References Cited

U.S. PATENT DOCUMENTS 3,138,615  6/1964  Bluestone .................... 260/326 C

*Primary Examiner*—Ethel G. Love
*Attorney, Agent, or Firm*—William H. Magidson; Arthur G. Gilkes; William T. McClain

[57] ABSTRACT

7,8-Diacyl bicyclo[2.2.2]oct-5-ene-bis(2,3-dicarboximide) and 7,8-diacyl bicyclo[2.2.2]octane-bis(2,3-dicarboximide) compounds useful for the production of polyimides.

4 Claims, No Drawings

7,8 DIACYL BICYCLO[2.2.2]BIS(2,3-DICARBOXIMIDE) COMPOUNDS

This invention relates to 7,8-diacyl bicyclo[2.2.2]octo-5-ene-bis (2,3-dicarboximide) and 7,8-diacyl bicyclo[2.2.2]octane bis(2,3-dicarboximide). More particularly, this invention relates to 7,8-dicarboxy bicyclo[2.2.2]oct-5-ene-bis(2,3-dicarboximide) and 7,8-dicarboxylic acid anhydride of bicyclo[2.2.2]oct-5-ene-bis(2,3-dicarboximide).

U.S. Pat. No. 3,553,231 discloses that bicyclo[2.2.2-]oct-5-ene-bis(2,3-dicarboximide) compounds are useful as central nervous system depressants. The patent indicates that these compounds can be substituted with lower alkyl, phenyl, halophenyl, lower alkoxyphenyl and trifluoromethylphenyl groups.

The object of this invention is to provide new bicyclo[2.2.2]bis(2,3-dicarboximide) compounds. Other objects of this invention appear hereinafter.

We have now found a new class of bicyclo[2.2.2]-bis(2,3-dicarboximide) compounds which are substituted at the 7 and 8 positions with acyl groups. These compounds may be useful in the same manner as bicyclo [2.2.2]oct-5-ene-bis(2,3-dicarboximide) compounds of U.S. Pat. No. 3,553,231 and are useful for the production of polyimides. In the production of polyimides, these compounds can be used in relatively low concentrations in reactions with tri- or tetra-functional acid compounds, such as trimellitic anhydride or pyromellitic anhydride, and diamines such as ethylene diamine, hexamethylene diamine, para-phenylene diamine, oxybisaniline, etc. and in some cases with glycols such as ethylene glycol, hexamethylene glycol, etc. These compounds can be represented by the structures:

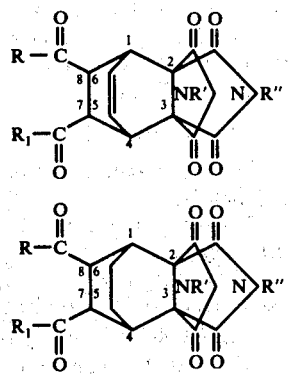

wherein R and $R_1$ are OH, $OR_2$, O-M/n, $NH_2$, $NHR_2$, $NR_2R_3$, M is an alkali metal (sodium, potassium, etc.), alkaline earth metal (calcium, barium, strontium, etc.) or a transition metal, n is an integer equal to the valence of the metal, $R_2$ and $R_3$ are alkyl groups of from 1 to 24 carbon atoms (methyl, tetracosyl, etc.), alkenyl of from 2 to 24 carbon atoms (vinyl, allyl, oleyl, etc.), aralkyl of from 7 to 25 carbon atoms (benzyl, octadecylbenzyl, etc.) aryl of from 6 to 24 carbon atoms (phenyl, paraoctadecylphenyl, etc.), R and $R_1$ taken together can be —O—, —NH or —NR''', R' and R'' can be alkyl groups of 1 to 24 carbon atoms (methyl, tetracosyl, etc.), R''' can be the same as $R_2$.

The compounds of this invention can be produced by essentially a two step process. In the simplest case, a 1,2-dihydrophthalic acid compound is reacted with tetracyanoethylene to form a Diels-Alder adduct of the type described in our paper (S. A. Cerefice and E. K. Fields, Amer. Chem. Soc. Div. Petrol. Chem. Preprints, 18, No. 1, 161 (1973), which is incorporated by reference. The cyano groups of the Diels-Alder adduct is then hydrolyzed to the bis(2,3-dicarboximide) compound in aqueous acid.

In those cases where the 7,8 diacyl derivatives are carboxy esters of monohydroxy compounds, it is generally desirable to carry out the Diels-Alder condensation of tetracyanoethylene with the appropriate diester of dihydrophthalic acid or form the diester from the Diels-Alder adduct. In those cases where the 7,8-dicarboxy acid or anhydride is desired, either dihydrophthalic acid or dihydrophthalic acid anhydride can be employed advantageously in the Diels-Alder reaction.

In any case, the bicyclo[2.2.2]bis(2,3-dicarboximide) can be produced from the tetracyanoethylene Diels-Alder adduct by heating the 7,8-diacyl bicyclo[2.2.2-]oct-5-ene-2,2,3,3-tetracarbonitrile in an aqueous acid solution of a strong acid at a temperature of about 80° C. to about reflux, for a period of about 1 to 20 hours. The insoluble dicarboximide can be collected by filtration, followed by washing with water and drying. The aqueous acid solution can comprise a dilute solution of any strong acid (mineral or organic) or mixture thereof. Suitable acids include sulfuric acid (e.g. 25 normal), mixtures of hydrogen bromide, acetic acid and water, and mixtures of hydrogen chloride, acetic acid and water, etc.

As indicated above, the dihydrophthalic acid derivatives useful in the Diels-Alder reaction include dihydrophthalic acid, dihydrophthalic anhydride, diesters of dihydrophthalic acid, esters of dihydrophthalic acid containing from 1 to 25 carbon atoms in the hydroxy moiety, etc.

The 1,2-dihydrophthalate esters suitable for producing the Diels-Alder adduct include the alkyl esters of 1,2-dihydrophthalic acid containing from 1 to 24 carbon atoms in each alkyl group, such as the dimethyl ester, the diethyl ester, the di-n-propyl ester, the di-isopropyl ester, the di-butyl ester, the di-(n-octyl) ester, the di(2-ethylhexyl) ester, the di-(n-tridecyl) ester, the di-stearyl ester, the ditetracosyl ester, the n-butyl 2-ethylhexyl ester, the diomega chloro-n-octyl ester, etc.; dialkenyl esters containing from 2 to 24 carbon atoms in each alkenyl group, such as the divinyl esters, the diallyl esters, the dioleyl esters, etc.; the diaryl esters containing from 6 to 24 carbon atoms, such as diphenyl, di(toluyl), the di(octadecylphenyl) ester, aralkyl esters containing from 7 to 25 carbon atoms, such as the benzyl ester, chlorobenzyl ester, etc.; mixed esters of two or more of the above types such as the benzyl octyl ester, etc.

The 1,2-dihydrophthalate esters can be produced by reacting the appropriate 1,2-dihydrophthalic acid compound (free acid, acyl halide or anhydride) with a suitable monohydroxy compound at a temperature of 60° to 200° C. or the dimethyl ester can be produced first and the appropriate diester produced by transesterification with a suitable monohydroxy compound at a temperature of 60° to 200° C.

Suitable monohydroxy compounds useful for producing the 1,2-dihydrophthalates include alcohols containing from 1 to 24 carbon atoms such as methyl alcohol, ethyl alcohol, isopropyl alcohol, allyl alcohol, methallyl alcohol, n-butyl alcohol, n-hexyl alcohol, n-octyl alcohol, 2-ethylhexyl alcohol, decyl alcohol, tridecyl alcohol, stearyl alcohol, oleyl alcohol, tetracosyl alcohol; aromatic hydroxy compounds containing from 6 to 24 carbon atoms, such as phenol, cresol, para-stearylphenol, napthol, etc., benzyl alcohol, etc.

These esters can be produced under conventional reaction conditions by reacting from about 1 to 10 moles of monohydroxy compound per carboxyl equivalent of said dihydrophthalic acid compound to form a solution of ester and monohydroxy compound. If desired esterification catalysts or transesterification catalysts can be used, such as sulfuric acid, phosphoric acid, paratoluene sulfonic acid, benzene sulfonic acid, stannous octoate, boron trifluoride etherate, tetraalkyl titanates and zirconates of U.S. Pat. No. 3,056,818.

In those cases where 7,8-dicarboximides or 7,8-dicarboxamides are desired the 7,8-dicarboxy or dianhydride of the bicyclo[2.2.2]oct-5-ene (2,3-dicarboximide) compounds can be reacted under conventional conditions with ammonia, primary amines or secondary diamines to produce either imides or amides. Amides can be produced using any of these classes of materials while imides can be formed with ammonia or primary amines.

In those cases where N or N,N' substituted 2,3-carboximides are desired, the compounds can be reacted with potassium hydroxide or potassium tert-butoxide in a solvent such as tert-butanol or dimethylsulfoxide at 0°–50° C to form potassium salts of the imides and then the potassium salts reacted with alkyl halides or aralkyl halides in the same solvents at 0°–80° C. for 0.5–50 hours. Alternatively, the 2,3-carboximides can be reacted with an excess of a primary alkyl, aryl, or aralkyl amine at 50°–150° C for 1–50 hours neat or in a solvent such as dimethyl formamide, dimethyl sulfoxide, or a hydrocarbon solvent (xylene, toluene, etc.) of suitable boiling point.

The various 7,8-diacyl bicyclo[2.2.2]oct-5-ene-bis-(2,3-dicarboxamide) compounds can be hydrogenated to form the corresponding 7,8-diacyl bicyclo[2.2.2]octane-bis-(2,3-dicarboxamide) compounds by hydrogenation of any of the aforesaid compounds except the 7,8-dicarboxy compound. This latter compound can be produced by hydrogenation of the 7,8-dianhydride followed by hydrolysis of the anhydride linkage after hydrogenation.

In somewhat greater detail, these compounds can be formed by treating an aqueous alkaline solution or dispersion of the oct-5-ene compound under 1 to 5 atmospheres of hydrogen at a temperature of from about 0° to 100° C. for from about 1 to 72 hours with a catalyst, such as palladium-on-charcoal, a platinum catalyst, a Raney nickel catalyst, etc. After the take up of hydrogen is complete, the catalyst can be separated by filtration and the filtrate acidified to precipitate the hydrogenation product.

The following examples are merely illustrative.

EXAMPLE I

A solution of 20 ml of 36 normal sulfuric acid in 20 ml of water was added to 5.56 grams of 7,8-dicarboxylic acid anhydride of bicyclo[2.2.2]oct-5-ene-2,2,3,3-tetracarbonitrile in a 100 ml one-necked flask equipped with a reflux condenser and stirrer. After the mixture was heated at 150° C. for 6 hours, the colorless product was cooled, filtered, washed with 400 ml of water and dried, yielding 2.31 grams of 7,8-dicarboxylic acid anhydride of bicyclo[2.2.2]oct-5-ene-bis-(2,3-dicarboximide), a 37% yield based on the starting material. The crude product was recrystallized from acetone and yielded a product melting at 360° C. The analysis calculated for $C_{14}H_8N_2O_7$ was 52.89% carbon (53.17% theoretical) 2.46% hydrogen (2.55% theoretical) and 8.74% nitrogen (8.86% theoretical).

The 7,8-dicarboxylic acid anhydride of bicyclo[2.2.2-]oct-5-ene-2,2,3,3-tetracarbonitrile used in this example was prepared by refluxing 2 grams of a mixture of 1,2-dihydrophthalic acid (93.2% pure containing 6.8% by weight phthalic acid) in 25 ml acetic anhydride for 30 minutes to dissolve the 1,2-dihydrophthalic acid in a 100 ml one-necked flask equipped with reflux condenser and stirrer. After the acetic anhydride solution of 1,2-dihydrophthalic acid was cooled to room temperature, 6.55 grams tetracyanoethylene was added and the resulting mixture maintained at 50° C. for 5 days. The white crystals which precipitated during heating, were filtered and washed with benzene yielding 12.43 grams (88% yield based on the tetracyanoethylene added) of 7,8-dicarboxylic acid anhydride of bicyclo[2.2.2]oct-5-ene-2,2,3,3-tetracarbonitrile (melting point 300° C. decomposition).

EXAMPLE II

This example illustrates conversion of the 7,8-dicarboxylic acid anhydride group to the 7,8-dicarboxylic acid group. A solution of 6.3 ml of 36 normal sulfuric acid in 13.7 ml of water was added to 2.78 grams of the bicyclo[2.2.2]oct-5-ene-bis(2,3-dicarboximide)-7,8-dicarboxylic anhydride of Example I in a 100 ml one-necked flask equipped with a reflux condenser and stirrer. The mixture was refluxed for 3½ hours, cooled, filtered, washed with 40 ml of cool water and dried to yield 1.28 grams of the 7,8-dicarboxylic acid compound (38% theoretical yield based on the starting anhydride). The compound did not melt on heating up to 360° C. but lost water to form the starting anhydride again at 225° to 230° C. The crude product was purified by recrystallization from water. The analysis calculated for the dicarboxylic acid ($C_{14}H_{10}N_2O_8$) was 50.40% carbon (50.31% theoretical), 2.76% hydrogen (3.02% theoretical) 8.51% nitrogen (8.35% theoretical).

EXAMPLE III

This example illustrates a second method of producing bicyclo[2.2.2]oct-5-ene-bis(2,3-dicarboximide)-7,8-dicarboxylic acid from the dianhydride. In this case 2.27 grams of the anhydride and 50 ml of water were refluxed for about 1½ hours in a 100 ml one-necked flask equipped with stirrer and reflux condenser. After refluxing for 1½ hours all the solids were in solution, the solution was concentrated to 25 ml on a rotary evaporator, heated to reflux again to dissolve the solids and allowed to cool to crystallize. Colorless crystals of the dicarboxylic acid were obtained by filtration of the cooled reaction mixture, yielding 218 grams (91% of the theoretical yield) of the dicarboxylic acid.

EXAMPLE IV

The dimethyl ester of 7,8-dicarboxylic acid anhydride of bicyclo[2.2.2]oct-5-ene-bis(2,3-dicarboximide) is prepared in the same manner as Example I using 5.56 grams of the dimethyl ester of 7,8-dicarboxylic acid bicyclo[2.2.2]oct-5-ene-2,2,3,3-tetracarbonitrile in place of the 7,8-dicarboxylic acid anhydride of Example I. The diester of 7,8-dicarboxylic acid of bicyclo[2.2.2-]oct-5-ene-2,2,3,3-tetracarbonitrile was prepared by refluxing 3 grams of the Diels-Alder adduct prepared in paragraph 2 of Example I in 50 ml of water until all the solids dissolved. The solution was cooled to 0° C. and filtered to yield 70% of the diacid hydrate which melted at 295° C. Two grams of the diacid in 25 ml methanol and 2 ml BF$_3$·ethyl ether was refluxed for 16 hours to produce 2.37 grams of the dimethyl ester after recrystallization from benzene. The dimethyl ester of 7,8-dicarboxylic acid bicyclo[2.2.2]oct-5-ene-2,2,3,3-tetracarbonitrile melted at 181° at 183° C.

Essentially the same results were obtained when the 1,2-dihydrophthalic anhydride was esterified with methanol in acetic anhydride using a BF$_3$ etherate catalyst system prior to the Diels-Alder addition of the dimethyl ester of 1,2-dihydrophthalic acid with tetracyanoethylene.

We claim:
1. A compound selected from the group consisting of 7,8-diacyl bicyclo[2.2.2]oct-5-ene-bis(2,3-dicarboximide) and 7,8-diacyl bicyclo[2.2.2]octane-bis(2,3-dicarboximide).
2. The compound of claim 1 having the structure 7,8-dicarboxy bicyclo[2.2.2]oct-5-ene-bis(2,3-dicarboxamide).
3. The compound of claim 1 having the structure dimethyl ester of 7,8-dicarboxy bicyclo[2.2.2]oct-5-ene-bis(2,3-dicarboximide).
4. The compound of claim 1 having the structure 7,8-dicarboxylic acid anhydride bicyclo[2.2.2]oct-5-ene-bis(2,3-dicarboximide).

* * * * *